United States Patent
Jardel et al.

(10) Patent No.: US 10,875,801 B2
(45) Date of Patent: Dec. 29, 2020

(54) SOLID-STATE ANAEROBIC DIGESTION METHOD

(71) Applicant: SBM DEVELOPPEMENT, Ecully (FR)

(72) Inventors: Denis Jardel, Saint Etienne la Thillaye (FR); Henri Frima, Saint Bernard (FR); Mohammed Benbrahim, Turckheim (FR)

(73) Assignee: SBM DEVELOPMENT, Ecully (FR)

( * ) Notice: Subject to any disclaimer, the term of this patent is extended or adjusted under 35 U.S.C. 154(b) by 243 days.

(21) Appl. No.: 15/577,018

(22) PCT Filed: Jun. 10, 2016

(86) PCT No.: PCT/FR2016/051398
§ 371 (c)(1),
(2) Date: Nov. 27, 2017

(87) PCT Pub. No.: WO2016/198798
PCT Pub. Date: Dec. 15, 2016

(65) Prior Publication Data
US 2018/0141841 A1    May 24, 2018

(30) Foreign Application Priority Data
Jun. 12, 2015  (FR) .................................. 15 55339

(51) Int. Cl.
*C02F 3/28*      (2006.01)
*C12P 5/02*      (2006.01)
*C02F 103/20*    (2006.01)
*C02F 103/26*    (2006.01)

(52) U.S. Cl.
CPC ............ *C02F 3/2806* (2013.01); *C12P 5/023* (2013.01); *C02F 2103/20* (2013.01); *C02F 2103/26* (2013.01); *C02F 2301/10* (2013.01); *C02F 2301/106* (2013.01); *Y02E 50/30* (2013.01)

(58) Field of Classification Search
CPC .............. C02F 3/2806; C02F 2301/106; C02F 2301/10; C02F 2103/20; C02F 2103/26; C12P 5/023; Y02E 50/343
See application file for complete search history.

(56) References Cited

U.S. PATENT DOCUMENTS

2013/0065290 A1 * 3/2013 Mate ...................... C02F 11/04
                                                        435/167

FOREIGN PATENT DOCUMENTS

| DE | 102009050867 A1 | 4/2011 |
| EP | 0173340 A2 | 3/1986 |
| EP | 1577269 A1 | 9/2005 |

OTHER PUBLICATIONS

Montalvo et al. "Application of natural zeolites in anaerobic digestion processes: A review" Apr. 2012, Applied Clay Science, vol. 58 pp. 125-133 (Year: 2012).*

(Continued)

*Primary Examiner* — Anthony J Zimmer
*Assistant Examiner* — Syed T Iqbal
(74) *Attorney, Agent, or Firm* — Oliff PLC

(57) ABSTRACT

The invention relates to a novel dry-state anaerobic digestion method comprising pretreatment of the input with an additive selected from among zeolite, clay, pozzolan and biochar.

8 Claims, 4 Drawing Sheets

: Cumulative production of biogas as a function of the particle size and the concentration of zeolite in the substrate

(56) References Cited

OTHER PUBLICATIONS

Kotsopoulos et al., "The impact of different natural zeolite concentrations on the methane production in thermophilic anaerobic digestion of pig waste," Biosystems Engineering, 2008, vol. 9, pp. 105-111.
Ho et al., "Mitigating ammonia inhibition of thermophilic anaerobic treatment of digested piggery wastewater: Use of pH reduction, zeolite, biomass and humic acid," Water Research, 2012, vol. 46, pp. 4339-4350.
Montalvo et al., "Use of natural zeolite at different doses and dosage procedures in batch and continuous anaerobic digestions of synthetic and swine wastes," Resources, Conservation and Recycling, 2006, vol. 47, pp. 26-41.
Sep. 2, 2016 Written Opinion issued in International Patent Application No. PCT/FR2016/051398.
Sep. 2, 2016 International Search Report submitted within International Patent Application No. PCT/FR2016/051398.
Montalvo S. et al., "Effect of particle size and doses of zeolite addition on anaerobic digestion processes of synthetic and piggery wastes", Process Biochemistry, vol. 40, No. 3-4, pp. 1475-1481, 2004.
Tada C. et al., "Effect of natural zeolite on methane production for anaerobic digestion of ammonium rich organic sludge", Bioresource Technology, vol. 96, No. 4, pp. 459-464, 2005.
Montalvo S. et al., "Application of natural zeolites in anaerobic digestion processes: A review", Applied Clay Science, vol. 58, pp. 125-133, 2012.

* cited by examiner

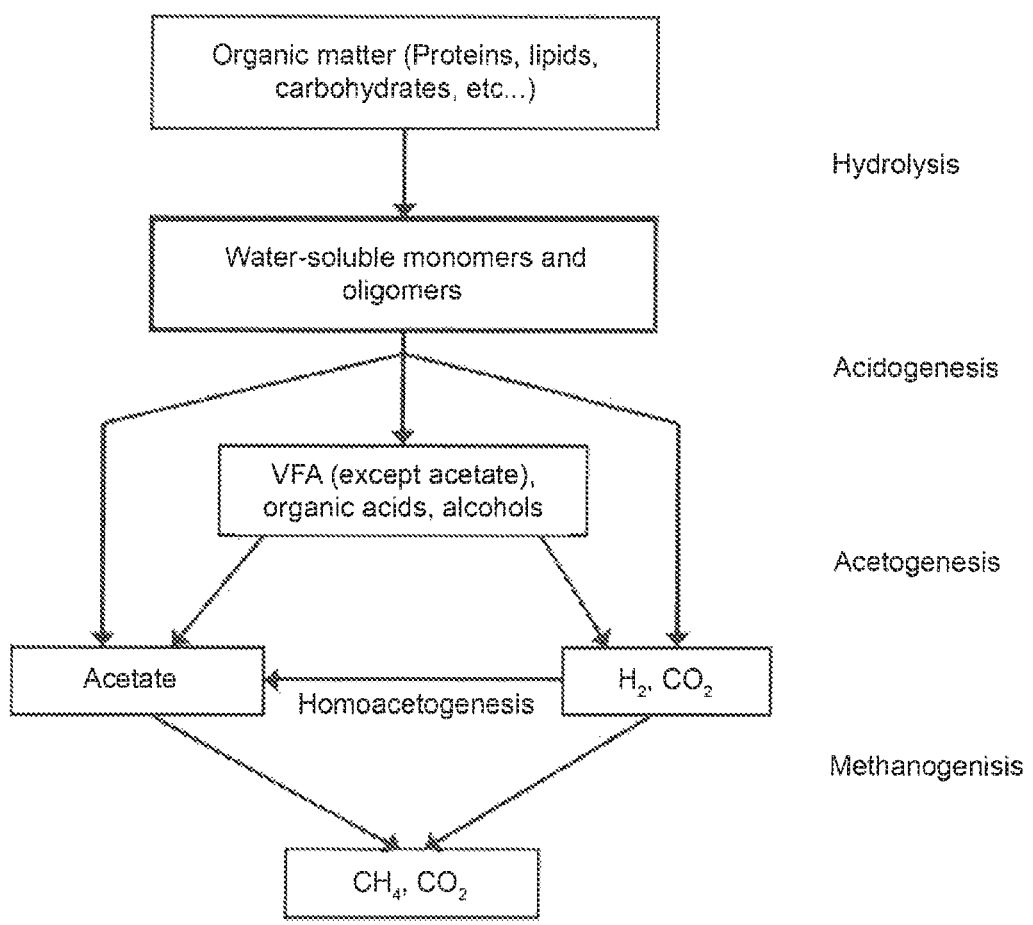
Figure 1: Methanization process

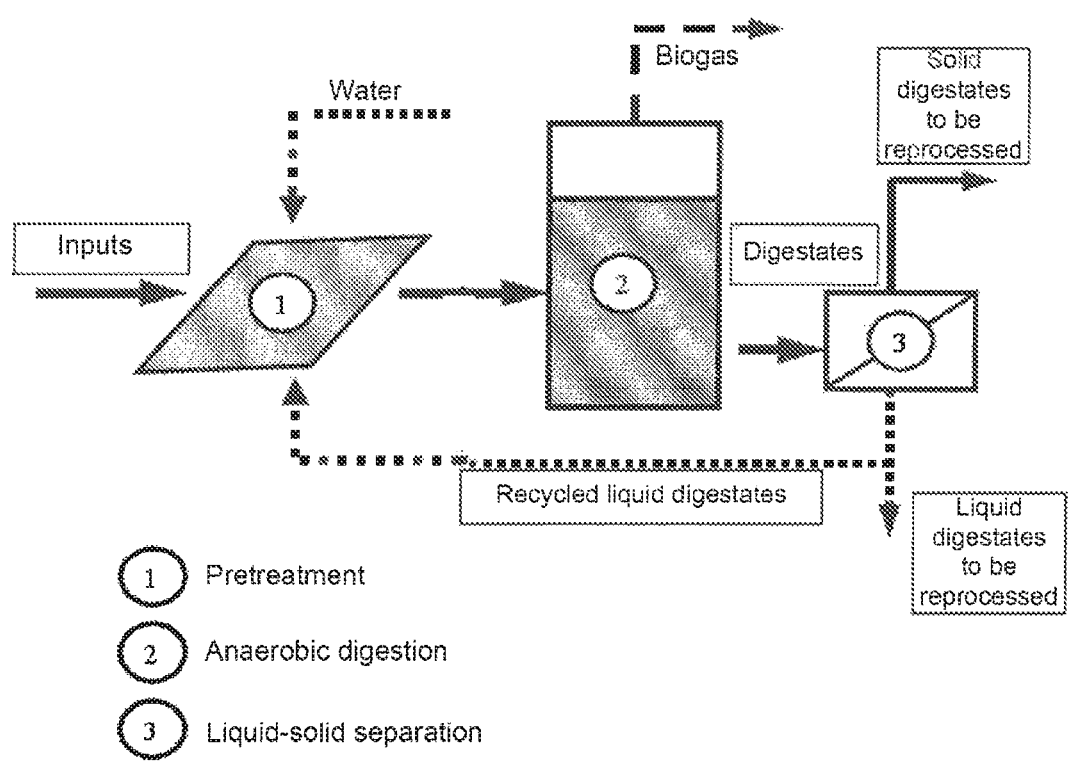
Figure 2: Methanization plant

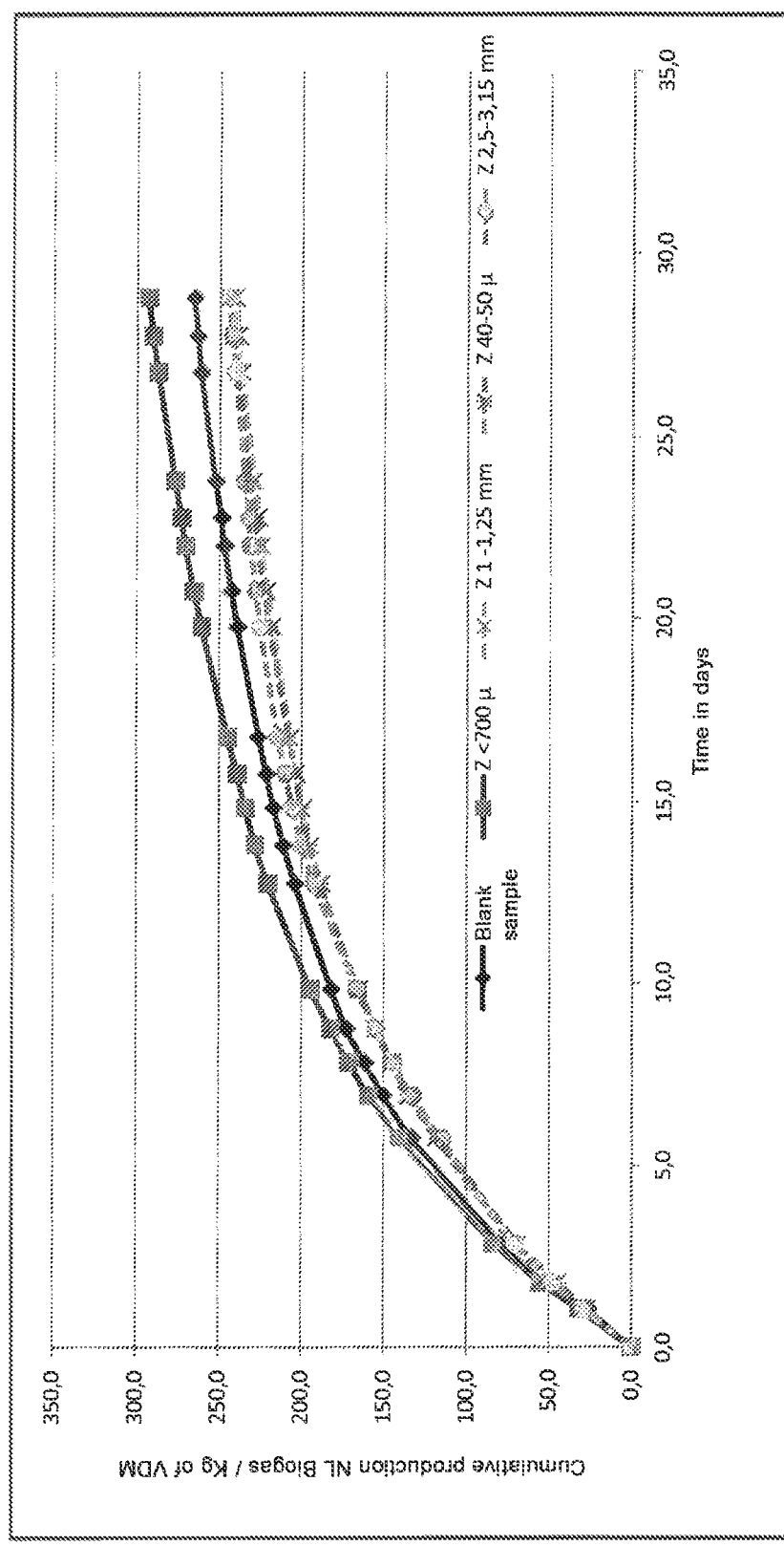
Figure 3: Cumulative production of biogas as a function of the particle size of zeolite

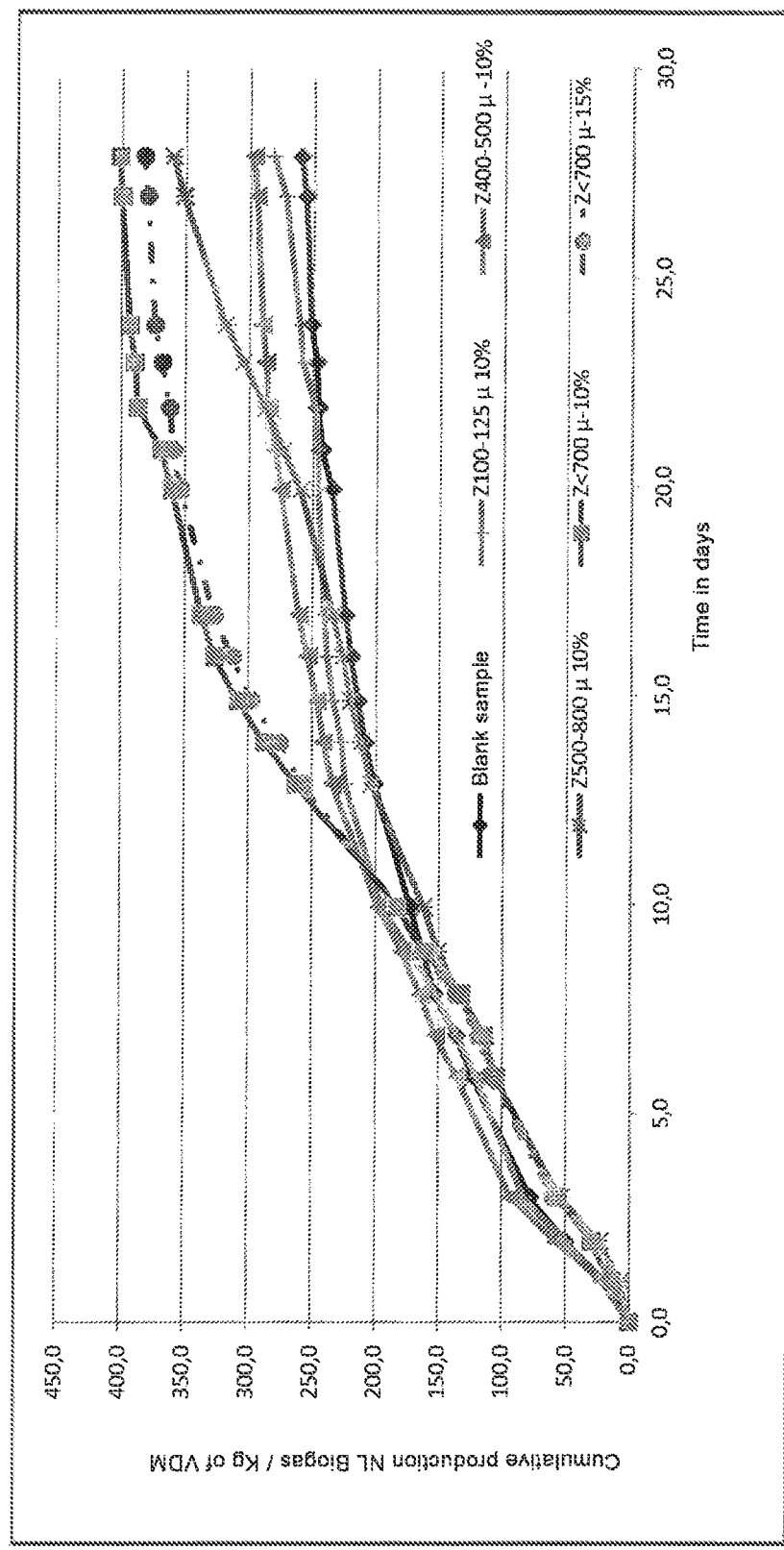
Figure 4 : Cumulative production of biogas as a function of the particle size and the concentration of zeolite in the substrate

SOLID-STATE ANAEROBIC DIGESTION METHOD

The object of the present invention is a new dry methanization process.

The methanization (or anaerobic digestion) is a natural biological degradation process of the organic matter in the absence of oxygen. It occurs naturally in some sediments, the swamps, the paddy fields, as well as in the digestive tract of some animals.

This biological process forms a stabilized digestion residue, called digestate, as well as a biogas of variable composition containing:
- between 50 to 80% of methane ($CH_4$);
- between 30 and 50% of carbon dioxide ($CO_2$);
- saturated water ($H_2O$);
- trace compounds ($NH_3$, $H_2S$, $N_2$, CO).

The methanization process is complex. The methanization is operated by several microbial populations which ensure the different phases (hydrolysis, acidogenesis, acetogenesis and methanization) of the anaerobic biodegradation of the organic matter. These microbial populations, present in the substrates, are very diverse and may be stimulated by organic or mineral additives. At least four groups of microorganisms are thus involved in the process: primary fermentative bacteria, secondary fermentative bacteria as well as two groups of methanogens.

The methanization process may be subdivided into four biochemical steps (FIG. 1):
- the hydrolysis, during which the biopolymers (proteins, lipids, carbohydrates, . . . ) are hydrolyzed into water-soluble monomers and oligomers thanks to extracellular enzymes excreted by microorganisms;
- the acidogenesis which is carried out by bacteria called acidogenic bacteria during which the products of the hydrolysis are transformed into volatile fatty acids (VFA) such as acetate, propionate or butyrate; into organic acids such as lactic acid or succinic acid; into hydrogen and into $CO_2$,
- the acetogenesis, which transforms the products of acetogenesis (except acetate) into acetate. It takes place according to two metabolisms: the acetogens which transform the organic acids into acetate, $CO_2$ and $H_2$; and the homoacetogens which combine hydrogen and $CO_2$ into acetate;
- the methanogenesis, the last step of the degradation process, forms methane according to two metabolisms. The acetotrophic methanogens transform the acetate into methane and $CO_2$, while the hydrogenotrophic methanogens transform hydrogen and $CO_2$ to form methane and water.

Each compound formed during one of these biochemical steps corresponds to the substrate used during the following step. Therefore, this forms a trophic chain whose diagram is shown in FIG. 1.

If the sequence of biological reactions is known, the performance of each of them has a random character depending on factors, currently not totally identified and controlled.

The control of the methanization process allows producing methane from waste or crops. On an industrial scale, the production of biogas by methanization experiences a significant industrial development, in particular in Europe, in particular in order to meet specific requirements such as the production of gas usable as energy from (solid or liquid) organic waste.

The methanization, as a bioprocess, may be implemented in a digester, in order to clean up waste loaded with organic matter while producing energy in the form of methane. The methanization allows processing waste as diverse as wastewater, sludges from sewage treatment plants, animal excrement, waste from agri-food industry, kitchen waste, household waste or still agricultural waste. The methanization with recovery of the produced biogas (production of thermal and/or electrical energy by direct combustion of methane or in heat engines) has its proper place among all the various solutions of renewable energy production by allowing reaching three complementary objectives: producing energy, reducing the pollutant load of waste and effluents and also, depending on the nature of the starting product, producing a stabilized digestate usable as a fertilizer, organic soil conditioner or fertilizer.

The methanization of solid waste is applied to most organic waste. This technique is applied to the fermentable fraction of the waste which must be sorted and collected by a separate collection, before being methanized. Depending on the source, different types of waste are distinguished:
- municipal waste such as food waste, newspapers, packaging, textiles, green waste or by-products of urban sanitation;
- industrial waste such as sludges from agri-food industries, processing waste from vegetable and animal industries or the fermentable fraction of the ordinary industrial waste (OIW);
- agricultural waste such as animal excrement, solid vegetable substrates or wood chips;
- littoral waste such as green algae.

The methanization may also be applied to dedicated crops such as maize.

There is a large number of industrial methanization processes. Their operation may be of continuous, discontinuous or semi-continuous type. The processes also differ depending on the types of pretreatments, the temperature regimes in which they are operating, the types of agitation and post-treatments. However, the general operation diagram remains identical, as illustrated in FIG. 2.

Between the input and the output of the methanization plant, the material will undergo successive steps of pretreatments (1), digestion (2) and liquid-solid separation (3) (FIG. 2). The flow of organic matter will undergo a transformation which will eventually lead to three types of products: liquid, solid and gaseous. In most recent industrial plants, and in particular in the plants operating by dry process, the liquid-solid separation may be followed by a post-treatment step of the digestion residues, for example a drying using the calories generated by the cogeneration.

To date, the existing plants for the implementation of the methanization, in particular «solid» or «dry» methanization, remain at the limit of the economic break-even point.

The production of biogas by the processes called «dry» processes is indeed affected by multiple factors and in particular the nature of the seasonal inputs and the inhibition of the anaerobic methanization by the excess production of disturbing compounds such as ammonia or the volatile fatty acids (VFA).

A reflection is engaged to search means for regularizing the methanization process either by acting on the avoidance of the excess production of disturbing compounds, thus by regulating the reaction medium and by keeping an optimal production of biogas; or by promoting/stimulating the development and the multiplication of microorganisms allowing increasing the microbial activities in the substrate and consequently the production of biogas.

This reflection also integrates the need for a favorable economic balance between the cost of the improvement means to be implemented and the result on the production of biogas, main source of income, with possibly the improvement of the agronomic value of the digestates which are then reused in agriculture in order to bring organic matter to soil and nutrients to crops.

The use of zeolite to increase the methane production within the scope of wet methanization has already been studied.

Thus, different authors have reported the use of zeolite during the methanization process of wastewater, in particular the pig slurry.

In «The impact of different natural zeolite concentrations on the methane production in thermophilic anaerobic digestion of pig waste», *Biosystemes Engineering*, 99, 2008, 105-111, Kotsopoulos and al. studied the effect of zeolite on the methanization of the pig slurry under thermophilic conditions and showed an increase in the production of biogas.

In «Application of natural zeolites in anaerobic digestion processes: A review», *Applied Clay Science*, 58, 2012, 125-133, Montalvo and al. have also demonstrated that the addition of zeolite at the dose of 1 g/l during the methanization process applied to pig excrement was increasing the degradability of the organic matter and the biogas production.

Finally, in «Mitigating ammonia inhibition of thermophilic anaerobic treatment of digested piggery wastewater: Use of pH reduction, zeolite, biomass and humic acid», *Water Research*, 46, 2012, 4339-4350, Ho and al. showed that the addition of zeolite to the slurry and sludges from sewage treatment plant at doses of 10 to 20 g/l was increasing the production of the biogas.

All of these publications suggest that the effect of zeolite on the production of the biogas during the wet methanization might be attributed to its role as a physical support for the microorganisms in low-solids liquid effluents as well as to an inhibition effect of the methanization by the ammonium ion that it contains, in particular for these effluents rich in nitrogen. To do this, zeolite is added to the effluent directly in the methanizer.

Furthermore, in «Effect of particle size and doses of zeolite addition on anaerobic digestion processes of synthetic and piggery wastes», *Process Biochemistry*, 40, 2005, 1475-1481, Montalvo and al. explain that the larger the diameter of the used zeolite particles is, the greater the contact surface is and the better the efficiency of the wet methanization process is.

Nevertheless, neither of these publications suggests that the zeolite addition might be made before the introduction of the input into the methanizer nor that the results obtained might be transposable to a dry methanization using, for example, inputs based on manure which is straw or containing a significant proportion of woody carbon. Indeed, such inputs themselves represent a potential physical support for microorganisms. Furthermore, being poorer in nitrogen than slurry, these inputs are less likely to cause an inhibition of the methanization via ammonium. Consequently, the addition of zeolite on this type of inputs did not seem a priori to be capable of improving the production of the biogas during the methanization. In addition, nothing in these publications would have incited those skilled in the art to work with a zeolite having a fine particle size rather than with a zeolite having a coarser particle size.

But, now it has been found, surprisingly, a new dry methanization process comprising a pretreatment of the waste by the addition of an additive of zeolite-type having a particular particle size (100 µm to 1000 µm) which allows significantly increasing the production of methane and improving the economic profitability of the process.

The object of the present invention is therefore a dry methanization process comprising the following steps:
a) pretreatment of the input comprising the addition of an additive selected from zeolite, clay, pozzolana and biochar whose particle size is comprised between 100 µm and 1000 µm followed or preceded by a hydrolysis;
b) anaerobic digestion;
c) separation of the solid phase and the liquid phase of the digestate.

Surprisingly, the process according to the present invention allows significantly increasing the methane production in comparison with the conventionally used processes, while improving their economic profitability.

In the context of the present invention:

«dry methanization process» means any process carried out on inputs (also called substrates, waste or effluents) having a dry material content greater than or equal to 20% at the input of the process allowing the production of biogas, in particular of methane, and a digestate;

«input», «waste» or «effluent» means the organic substances with methanogenic capacity used for the load of the methanization plant, such as the slurries or manures, the vegetable matter, the organic matter or the organic matter vegetable waste (coming from the agriculture, the agri-food industry, the catering), of sludges or effluents from sewage treatment plants;

«digestate» means any residual substance in liquid, pasty or solid form present in the digester at the end of the methanization process and generally consisting of excess bacteria, non-degraded organic matter, mineralized matter and water;

«dry material» means any raw material composed of mineral and organic matter dried at 100° C. to a constant weight;

«dry material content» means the ratio p/p, expressed in %, of the materials after drying (DM)/raw materials before drying;

«zeolite» means any zeolite known to those skilled in the art, whether natural or synthetic. Preferably, the term zeolite refers to a natural zeolite selected from the family of analcimes such as analcime, pollucite, wairakite, bellbergite, bikitaite, boggsite and brewsterite; the family of chabazites such as chabazite, willhendersonite, cowlesite, dachiardite, edingtonite, epistilbite, erionite, faujasite, ferrienite and herschelite; the family of gismondines such as amicite, garronite, gismondine, gobbinsite, gmelinite, gonnardite and goosecreekite; the family of harrnotornes such as harmotome, phillipsite and wellsite; the family of heulandites such as clinoptilolite, heulandite, laumontite, levyne, mazzite, merlinoite, montesommaite, mordenite and maricopaite; the family of natrolites such as mesolite, natrolite, scolecite, offretite, paranatrolite, paulingite and perlialite; the family of stilbites such as barrerite, stilbite, stellerite, thomsonite, tschernichite and yugawaralite; sodium dachiardite; and tetranatrolite. Still more preferably, the term zeolite refers to clinoptilolite, chabazite, phillipsite, ferrierite, mordenite or erionite. In a totally preferred manner, the term zeolite refers to clinoptilolite; and «clay» means any clay known to those skilled in the art. Preferably, the term clay refers to aluminum phyllosilicates whose sheets are constituted of layers of octahedra Al(OH)$_6$ and layers of tetrahedra SiO$_4$ linked by the O and OH atoms put in common and formed of fine particles of the order of the µm among which kaolinite (1/1), illite (2/1), smectite (2/1), glauconite, chlorite (2/1), vermiculite (2/1) and the fibrous clays such as sepiolite and attapulgite (or paligorskite). More preferably, the term clay refers to fibrous clays such as sepiolite and attapulgite. In a totally preferred manner, the term clay refers to sepiolite.

In the context of the present invention, «additive whose particle size varies from 'x' µm to 'y' µm» means any additive in the form of a powder whose at least 50% (in volume) of the particles have a diameter comprised between 'x' µm and 'y' µm, the particle diameter may be determined by any process known to those skilled in the art, in particular by screening.

Furthermore, in the context of the present invention, the proportions expressed in % correspond to weight percentages relative to the total weight of the considered entity (for example the dry material).

FIG. 1 shows the reaction scheme of the methanization process.

FIG. 2 shows a conventional plant for the implementation of the methanization process.

FIG. 3 shows the experimental results obtained during the measurement of cumulated biogas production as a function of the particle size of the used zeolite.

FIG. 4 shows the experimental results obtained during the measurement of cumulated biogas production as a function of the particle size and the zeolite concentration used in the substrate.

Step a) of the process according to the present invention therefore corresponds to a pretreatment step of the input comprising in particular the addition of an additive selected from zeolite, clay, pozzolana and biochar whose particle size ranges from 100 µm to 1000 µm followed or preceded by a hydrolysis.

Preferably, step a) of the process according to the present invention is conducted under the following conditions, taken alone or in combinations:
the additive is selected as the zeolite;
the particle size of the additive ranges from 400 µm to 900 µm; still preferably from 500 µm to 800 µm,
the additive is added in proportions ranging from 5% to 15% by weight of dry material of the inputs. More preferably, the additive is added in proportions ranging from 6% to 14% by weight of dry material of the inputs. In a totally preferred manner, the additive is added in proportions ranging from 7% to 12% by weight of dry material of the inputs;
the inputs are selected from straw manure (bovine, equine or any similar straw-based material), the seeds, the straw menu or the raw vegetables;
the dry material content of the input ranges from 20% to 90%, preferably from 28% to 55%;
the additive is added to the raw material (input) and mixed manually or with any appropriate means, allowing a homogeneous distribution of the additive in the substrate.
the mixture of the additive and the inputs is produced before the beginning of the hydrolysis phase,
the hydrolysis is carried out by adding water and/or recycled liquid digestate at the end of the separation step of the solid phase and the liquid phase of the digestate (step c) of the process according to the present invention—FIG. 2);
the temperature at which the addition of the additive and the inputs is carried out ranges from 20° C. to 37° C.;
the hydrolysis time varies from 24 h to 90 h; and/or
the temperature at which the hydrolysis is carried out varies from 20° C. to 55° C.

At the end of step a) of the process according to the present invention, the pretreated inputs (or substrates) are injected into a digester in order to undergo an anaerobic digestion (step b)).

The anaerobic digestion step may be conducted by any means known to those skilled in the art, in particular by the use of a vertical or horizontal digester.

Two temperature regimes are mainly used: mesophilic (from 30° C. to 40° C.) or thermophilic (from 45° C. to 60° C.).

The anaerobic digestion step b) is carried out in the presence of an inoculum added to the substrate, said inoculum capable of being any inoculum known to those skilled in the art adapted to the nature of the used input and to the methanization conditions. Preferably, step b) of the process according to the present invention is conducted under the following conditions, taken alone or in combinations:
the digester is of the horizontal type with a sealed piston type or «box» type feed, provided with systems of drainage, recirculation of «juices» by pumping and gas management;
the temperature regime is of the mesophilic or thermophilic type;
the stirring is ensured by recirculation of the juices or by a horizontal blade shaft whose rotation is sequenced to degas the substrate and facilitate the progress of the load; and/or
the temperature holding is ensured by a plate heat exchanger At the end of step b) of the process according to the present invention, the solid phase and the liquid phase are separated of the obtained digestate (step c) of the process according to the present invention).

The main function of this step is to separate a liquid fraction slightly loaded with dry material (DM) to be capable of bringing the inputs to the good dryness and to obtain solid digestates which can be handled without free juice or whose structure facilitates the air circulation in order to ensure the composting or possibly the drying with heated air thereof by heat recovery of cogeneration plant for example.

The solid phase and the liquid phase of the mixture obtained in step b) may be separated by any means known to those skilled in the art. In particular, it will be possible to use a filter press or proceed by gravity separation and extraction of the liquid phase.

Preferably, the digestates output from the anaerobic phase are directly introduced into the separator without pretreatment other than that specific to the particularities of the recipe or the installation.

At the end of the process according to the present invention, three distinct products are obtained;
biogas mainly consisted of carbon dioxide (between 30 and 50%) and methane (between 50 and 70%); water saturated and containing traces of gaseous impurities (NH$_3$, H$_2$S, N$_2$, CO);
a liquid phase containing water and solubilized salts and fine particles of dry material (DM). Generally the dry material content (DM) is lower than 7%; preferably comprised between 3 and 5% and are called «juices»;
and a solid phase constituted of coarse dry materials, with a high content of stable organic matter and still containing a quantitative majority of «juices» absorbed or adsorbed (generally from 65 to 72%). Generally, the solid phase is exempt of free «juices».

The non-recycled solid or liquid fractions containing organic matter and nutrients for the plants (mainly nitrogen, phosphorus and potassium) have a «waste» status and are usable in spreading plans for agriculture.

Nevertheless, the obtained digestates have some agronomic properties and are likely to support transformations to enrich them, and facilitate the storage, the handling and the dosage thereof at the application. The first transformation is generally a drying to concentrate the organic matter and the nutrients by using heat produced by the power generation. The product accordingly dried may be mixed with other fertilizing materials and transformed, for example, into granules.

The present invention is illustrated in a non-limiting manner by the following examples.

Example: Methanization Process According to the Invention

A—Experimental Protocol

1.1—Pretreatment (Step a)

1.1.1—Used Input

The used input is constituted of 79% of manure (straw horse manure) and 21% fresh vegetables (carrots, courgettes, green beans in substantially equal parts).

The manures were ground beforehand to obtain busted fibers of maximum length of 2 cm.

Vegetables, for their part, are cut so that their size varies from 1 to 2 cm.

1.1.2—Used Additive

The used additive is a natural zeolite of the clinoptilolite class (Aquavista Limited company), brand name TerraSorb™.

The grade <700 μm was tested as supplied.

The grade 1 to 3 mm was ground using a conventional hammer mill, then the ground sample was dry screened using a laboratory screening apparatus: RUSSEL Finex Screen vibrating screen—VSIA—A14550, with different stacked screen stages of the smallest mesh (lower row) to the largest mesh (top row), so as to have different, separate, identified particle sizes.

The used screens are the following:

| Mark | Mesh | Brand | Reference |
|---|---|---|---|
| 11 | 3.15 mm | SAULAS | NFX 11 |
| 10 | 2.5 mm | Prüfsieb | AFNOR 547037 |
| 9 | 1.25 mm | Prüfsieb | DIN 4188 |
| 8 | 1 mm | Prüfsieb | AFNOR NFX 11.501 |
| 7 | 800 μm | Prüfsieb | AFNOR NFX 11.501 |
| 6 | 500 μm | Prüfsieb | AFNOR NFX 11.504 |
| 5 | 400 μm | Prüfsieb | AFNOR NFX 11.501 |
| 4 | 125 μm | SAULAS | NFX 11.501 |
| 3 | 100 μm | Prüfsieb | AFNOR 11955 |
| 2 | 50 μm | SAULAS | AFNOR 18 |
| 1 | 40 μm | SAULAS | AFNOR 17 |

Within the scope of the assays which have been carried out, different zeolite particle sizes have been tested:

| Used zeolite | Assay reference |
|---|---|
| TerraSorb ™ grade 1 to 3 mm: ground natural zeolite, screened between screen marks 1 & 2 - Size 40μ to 50μ | Z 40-50μ |
| TerraSorb ™ grade 1 to 3 mm: ground natural zeolite, screened between screen marks 3 & 4 - Size 100μ to 125μ | Z 100-125μ |
| TerraSorb ™ grade 1 to 3 mm: ground natural zeolite, screened between screen marks 5 & 6 - Size 400μ to 500μ | Z 400-500μ |
| TerraSorb ™ grade 1 to 3 mm: ground natural zeolite, screened between screen marks 6 & 7 - Size 500μ to 800μ | Z 500-800μ |
| TerraSorb ™ grade<700μ: natural zeolite, commercial product | Z <700μ |
| TerraSorb ™ grade 1 to 3 mm: ground natural zeolite, screened between screen marks 8 & 9 - Size 1 mm to 1.25 mm | Z 1-1.25 mm |
| TerraSorb ™ grade 1 to 3 mm: ground natural zeolite, screened between screen marks 10 & 11 - Size 2.5 mm to 3.15 mm | Z 2.5-3.15 mm |

1.1.3—Pretreatment

The zeolite is manually and gradually mixed with the substrate to ensure a homogeneous distribution. Water is gradually added when mixing the additive and the substrate in order to obtain a substrate adjusted up to about 40% of dry material.

The zeolite is added in proportions of 5%, 10% or 15% of dry material according to the assay which is carried out.

The obtained substrate is subsequently stored at ambient temperature for about 32 hours prior to methanization. The hydrolysis phase takes place during this storage time.

1.2—Anaerobic Digestion (Step b)

1.2.1—Preparation of the Inoculum

The used inoculum comes from a pilot dedicated to the production of inoculum. This pilot is maintained in a continuous methanization in an infinitely mixed system (DM about 7%) and held at 54° C., with a regular and daily stirring. It is fed twice a week with a mixture of cereals, green waste and sludges from sewage treatment plants. The proportions of this mixture are 8 parts for the sludges, 1 part for the green waste, 1 part for the cereals, so as to obtain a substrate of about 7% of DM.

At each feed, the stirring is stopped and a known volume (from 5 to 15%) of the digestate is removed and replaced by an equivalent volume of the substrate. The output digestate constitutes the inoculum for the methanization assays.

Prior to the use of the inoculum, the inoculum is tested to determine its activity level and its capability to degrade the organic matter. For this assay, a known volume of inoculum is brought together with a known amount of acetate and put in thermophilic incubation for a duration of about 48 hours. The inoculum is considered active when at least 80% of the introduced acetate is degraded.

1.2.2—Anaerobic Digestion

The used digesters are PVC enclosures of about 1 liter or 6 liters manufactured specifically for the methanization. Each enclosure is provided with a feed cap and a biogas outlet orifice.

The substrate obtained in the previous step 1.1.3 is added into the digester, then inoculated with the inoculum obtained in the previous step 1.2.1. The added inoculum amount is about 39% of the total substrate amount present in the digester. Water is added in order to adjust the dry material content up to about 24%.

The temperature in the digester is held at 54° C. using a water bath. The mixture is manually and daily stirred (working days) for 2 to 3 minutes.

The produced biogas amount is measured once a day throughout the duration of the assay.

B—Obtained Experimental Results and Conclusions

2.1—Test 1—Particle Size of the Zeolite

The assay was carried out according to steps a) and b) described in the previous examples 1.1 and 1.2 under the following operating conditions:

| | |
|---|---|
| Volume of the used reactor (in l) | 1 |
| Amount of inputs (in g) | 83.3 |
| | (horse manure: 61 g/vegetables: 16.3 g/water: 6 g) |
| Amount of zeolite (% by weight of dry material of the inputs) | 10% (that being 2.7 g) |
| Amount of inoculum (in g) | 56 |

The Zeolites Z 40-50µ, Z<700µ, Z 1-1.25 mm and Z 2.5-3.15 mm were used.

Cumulative biogas production for each of these substrates was measured for 30 days and compared to that of a «blank sample» a substrate to which no zeolite was added.

The obtained results are reported in FIG. 3.

2.2—Assay 2—Particle, Size, and Concentration of the Zeolite

The assay was carried out according to steps a) and b) described in the previous examples 1.1 and 1.2 under the following operating conditions:

| | |
|---|---|
| Volume of the used reactor (in l) | 6.5 |
| Amount of digestate (in g) | 520 |
| | (Horse manure: 380 g/vegetables: 100 g/water: 40 g) |
| Amount of zeolite (% by weight of dry material of the inputs) | 10% (that being 21 g) or 15% (that being 31.5 g) |
| Amount of inoculum (in g) | 350 |

The zeolites Z 100-125µ, Z 400-500µ, Z 500-800µ and Z<700µ were used at different concentrations (10% or 15% by weight of dry mass of the inputs).

The cumulative biogas production for each of these substrates was measured for 30 days and compared to that of a «blank sample» substrate to which no zeolite was added.

The obtained results are reported in FIG. 4.

2.3—Conclusions

The provision of a zeolite of particle size greater than or equal to 100 µm and lower than or equal to 1000 µm allows accelerating the biogas production of an existing plant and thus increasing the daily charge in fresh waste; which results in an increase of produced energy(energies), recoverable in the same proportion to installation and constant fixed costs.

Furthermore, the addition of zeolite in a proportion ranging from 5% to 15% appears optimum in terms of efficiency relative to the cost.

The invention claimed is:

1. A dry methanization process comprising the following steps:
    a) pretreatment of an input, the pretreatment comprising the addition of an additive selected from zeolite, clay, pozzolana and biochar whose particle size is less than 700 µm followed or preceded by a hydrolysis, wherein the input is an organic substance with methanogenic capacity, and
    the additive is added in proportions ranging from 5% to 15% by weight of dry matter of the inputs;
    b) anaerobic digestion;
    c) separation of the solid phase and the liquid phase of the digestate; wherein production of biogas via the dry methanization process is carried out for a period of more than 10 days.

2. The process according to claim 1, wherein the additive is zeolite.

3. The process according to claim 2, wherein the zeolite is selected from clinoptilolite, chabazite, phillipsite, ferrierite, mordenite and erionite.

4. The process according to claim 3, wherein the zeolite is clinoptilolite.

5. The process according to claim 1, wherein the additive is added in proportions ranging from 7% to 12% by weight of dry matter of the inputs.

6. The process according to claim 1, wherein the additive is added in proportions ranging from 6% to 14% by weight of dry matter of the inputs.

7. The process according to claim 1, wherein in step a), the pretreatment is performed prior to the hydrolysis.

8. The process according to claim 1, wherein step b) is conducted under mesophilic or thermophilic conditions.

* * * * *